US00PP16917P2

(12) United States Plant Patent
Dirr

(10) Patent No.: US PP16,917 P2
(45) Date of Patent: Aug. 1, 2006

(54) CRAPEMYRTLE PLANT NAMED 'GAMAD I'

(50) Latin Name: *Lagerstroemia indica×L. fauriei*
Varietal Denomination: Crapemyrtle Gamad I

(75) Inventor: Michael A. Dirr, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 47 days.

(21) Appl. No.: 11/080,753

(22) Filed: Mar. 15, 2005

(51) Int. Cl.
*A01H 5/00* (2006.01)

(52) U.S. Cl. ..... Plt./252
(58) Field of Classification Search ..... Plt./252
See application file for complete search history.

(56) References Cited

PUBLICATIONS

Dirr, M. "Breeding offers crape myrtles with new flowers, form and color"; *Nursery Management & Production* (Apr. 2005), 21(4):12–13, 76–78.

*Primary Examiner*—Anne Marie Grunberg
*Assistant Examiner*—Georgia Helmer
(74) *Attorney, Agent, or Firm*—Greenlee Winner and Sullivan PC

(57) ABSTRACT

A new and distinct cultivar of crapemyrtle, *Lagerstroemia indica×L. fauriei*, which is characterized by compact-mounded growth habit; bronze-green emerging leaves, lustrous dark green in summer, yellow-orange-red in fall; high leaf powdery mildew and *Cercospora* leaf spot resistance; glossy red buds; cherry red flowers that are colorful from mid-July to early September in Athens, Ga.

3 Drawing Sheets

Botanical classification: *Lagerstroemia indica×L. fauriei.*
Varietal denomination: crapemyrtle Gamad I.

BACKGROUND OF THE INVENTION

The present invention relates to a new and distinct cultivar of the ornamental flowering shrub *Lagerstroemia indica× Lagerstroemia fauriei*, commonly known as crapemyrtle, and hereafter referred to by the varietal denomination 'Gamad I'.

The new crapemyrtle originated from open-pollinated seed of 'Pocomoke' (unpatented) a compact, rose-pink flowered introduction in 1999 from the United States National Arboretum (USDA). The inventor was granted permission by Dr. Margaret Pooler, Research Geneticist at USDA, to utilize the germplasm to develop new dwarf cultivars. 'Gamad I' was the only true red-flowered seedling from 2000 seedlings of 'Pocomoke' and was selected by the inventor in August, 2002 at the Center for Applied Nursery Research, Dearing, Ga.

SUMMARY OF THE INVENTION

Plants of the cultivar 'Gamad I' have not been observed under all possible environmental conditions. The phenotype may vary somewhat with variations in environment such as light-intensity, temperature and cultural conditions, however, without any variance in genotype.

The following characteristics have been consistently observed and, to the best knowledge of the inventor, are the unique characteristics of 'Gamad I' as a new and distinct cultivar.

1. Compact-mounded habit.
2. Bronze-green new leaves; glossy dark green at maturity; yellow-orange-red coloration in autumn.

3. High leaf mildew, *Cercospora* leaf spot and flea beetle resistances.
4. Glossy red buds open to cherry red flowers in mid to late summer.

Plants of the new crapemyrtle have been compared to the only true genetic dwarf crape myrtles known to the inventor, *Lagerstroemia* 'Chickasaw' (unpatented) and 'Pocomoke'. Comparative evaluations in containers and in the ground at Athens, Ga. showed that 'Gamad I' differed from 'Chickasaw' and 'Pocomoke' in the following characteristics:

1. Plants of 'Gamad I' produced true cherry red flowers compared to the pure lavender-pink flowers of 'Chickasaw' and the deep rose-pink flowers of 'Pocomoke'.
2. Plants of 'Gamad I' maintained cleaner, i.e. less diseased and flea beetle injured foliage than 'Chickasaw' and 'Pocomoke', into late October.
3. Plants of 'Gamad I' grew faster and filled the 11.8 liter containers faster than 'Chickasaw' and 'Pocomoke', yet maintained the dense, compact-mounded habit without pruning.
4. Plants of 'Gamad I' flowered about two weeks later than plants of 'Chickasaw' and 'Pocomoke' and remained effective into early September while 'Chickasaw' and 'Pocomoke' ceased flowering by mid August.

Asexual reproduction via tissue culture and by traditional vegetative cuttings since August 2002 in Athens, Ga. has shown that the unique characteristics of this new crapemyrtle are stable and reproduced true-to-type in successive generations.

BRIEF DESCRIPTION OF THE PHOTOGRAPHS

The accompanying colored photographs illustrate the unique characteristics of the new cultivar, showing the colors as true as it is reasonably possible to obtain in colored reproductions of this type. Colors in the photograph may differ from the color values listed in the detailed botanical description which accurately describe the colors of the new crapemyrtle.

DETAILED BOTANICAL DESCRIPTION

Figure 1:
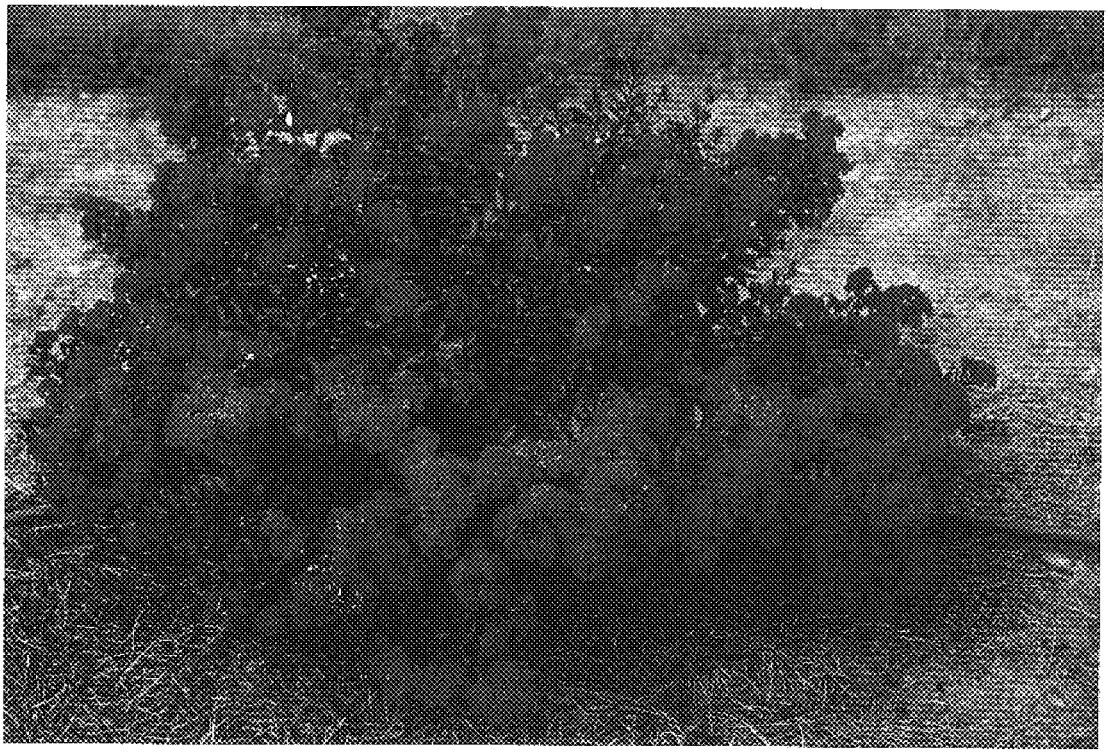
FIG. 1 Illustrates a two-year-old plant in the ground, Athens, Ga., August, 2004.
Figure 2:
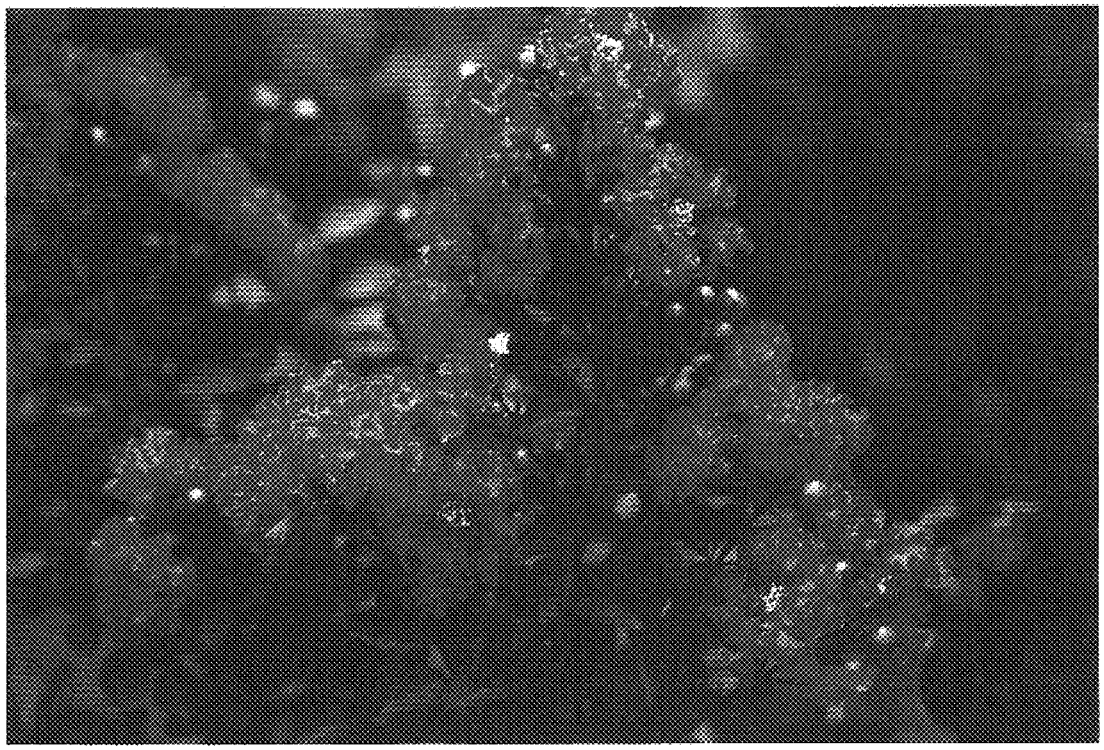
FIG. 2 Illustrates a close up showing flower buds, open flowers, flowers showing yellow stamens, and summer foliage.
Figure 3:
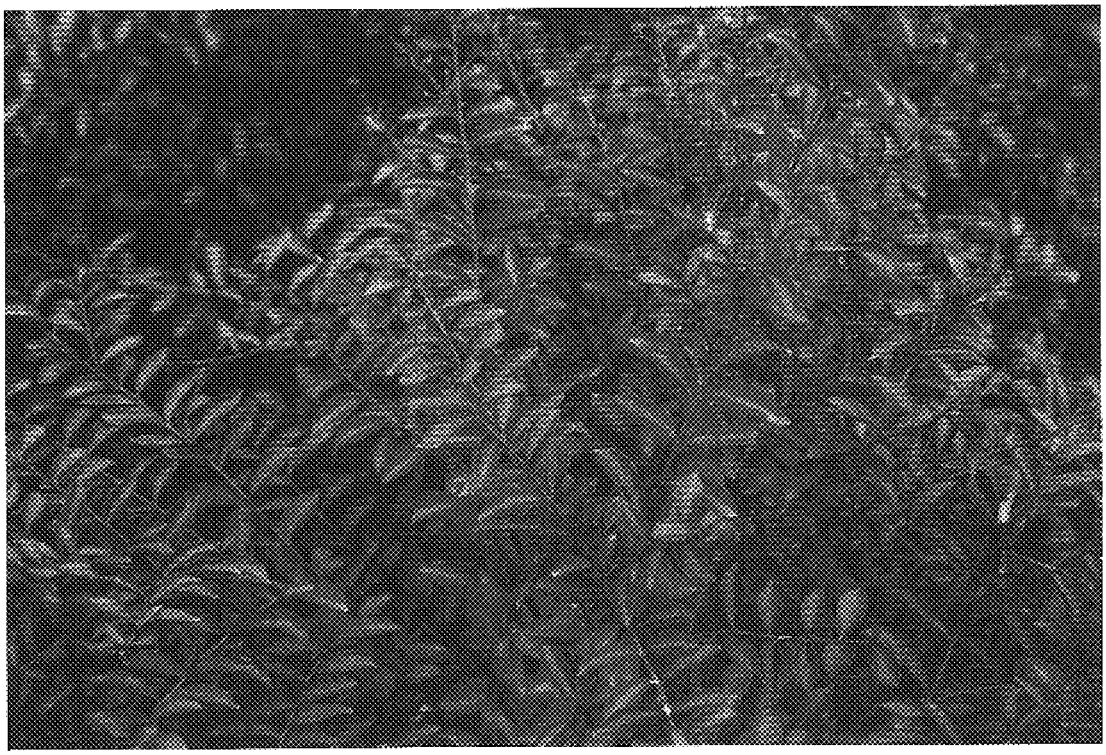
FIG. 3 Illustrates the fall foliage.

The botanical description of 'Gamad I' is based on three-year-old plants, growing in 22 liter containers in an outside nursery research facility in Athens, Ga. (USDA Zone 7b) under conditions which closely approximate commercial production. Measurements are based on the average of 10 to 20 samples, and were taken throughout the main growth period, from March through September in Athens, Ga. Colors are based on The Royal Horticultural Society Colour Chart, 1995 edition.

The plant has a compact mounded growth habit with extensive branching, attaining an average height of 73 cm. and width of 100 cm.

First year stems are round, 1.0 mm in diameter, with internode lengths of 3.5 to 13.5 mm. They are Grey-Brown, 199D in color, and the bark is exfoliating in strips.

Second year stems are 3 mm in diameter, with color Grey-Brown N 199D to Grey-Brown 199D with stripes of Brown 200C. The bark exfoliates in strips.

The vegetative buds are sub-opposite to alternate in arrangement, ovoid in shape, 3 mm in length and 1 mm in width, with no pubescence, and the bud scales are Grey-Brown N 199B in color.

The mature leaf, measured in the middle section of first year stems, averages 21 mm in length and 13 mm in width. The leaf is obovate, with an accuminate apex, acute base and entire margin. The emerging leaf (March–April in Athens, Ga.) is Greyed-Purple 183B to Yellow-Green N 144A to Yellow-Green N 144D on both upper and lower surfaces. In summer (July), the upper surface is Green 137A and the lower surface is Green 137C. In the fall (November), the leaves show a rainbow of colors, with the upper surfaces ranging from Yellow-Orange 16A to Yellow-Orange 21B to Red 53A to Greyed-Purple 187A and lower surface from Yellow-Orange 16C to Yellow-Orange 22B to Red 53B to Yellow-Green 146C.

The leaves are arranged sub-opposite to alternate on the stem and are leathery, thick and very shiny. The venation is pinnate and the vein color is Yellow-Green 144A. The petiole is 1 mm in length and 1 mm in diameter, oval in cross-section shape with fine pubescence and Yellow-Green 144A in color.

The shiny flower buds are 6 mm in length and 6 mm in width, round in shape with no pubescence, and are Greyed-Red 180A in color.

The flowering period is from mid July to early September in Athens, Ga. The inflorescence averages 7.5 cm in length and 6.7 cm in width, and a plant in a 11.8 liter container carries 25–30 inflorescences. The color is Red 53B in full bloom, fading to Red 46A. There are 15–20 flowers per inflorescence. The peduncle is finely pubescent and is Greyed-Purple 183C in color.

The petals average 2 cm in length by 1.5 cm in width, are fan-shaped with a ruffled, rounded apex, sagittate base and ruffled margin. There is no pubescence. The color of both upper and lower surfaces at peak of bloom is Red 53B.

The pedicels are 5 mm long, with no pubescence and are Greyed-Red 181A in color.

There are 20 to 30 stamens. The anther is 1 mm in length and 1 mm in width, and Yellow-Orange 14A in color. The filaments average 8 mm in length and 0.3 mm in width and are colored Red 39C at the top, fading to Yellow-White 158D at the base. The pollen in Yellow-Orange 14A in color.

The superior pistil is 1.5 cm in length and 0.5 mm in width. The stigma is round in shape, with no pubescence and Yellow-Green 148A in color. The style is 1.5 cm in length, round in shape, and Greyed-Red 179A in color, with no pubescence. There is a single ovary, oval to rounded in shape, with no pubescence.

The mature fruit is a six-valved dehiscent, broad ellipsoidal capsule, measuring 6 to 8 mm in length and 6 to 8 mm in width, prior to dehiscence. The color is Brown 200A. There are multiple seeds per capsule, averaging 6 mm long, and 3 mm wide, with a membraneous wing. The color of the seed is Brown 200A, and the wing is Grey-Brown 199D.

I claim:

1. A new and distinct cultivar of crapemyrtle plant named 'Gamad I', substantially as illustrated and described.

* * * * *